United States Patent [19]

Schneider et al.

[11] Patent Number: 4,561,942
[45] Date of Patent: Dec. 31, 1985

[54] ISOLATION OF METHYL 4-PENTENOATE FROM MIXTURES CONTAINING THIS AND METHYL 3-PENTENOATE

[75] Inventors: Heinz-Walter Schneider, Ludwigshafen; Rudolf Kummer, Frankenthal; Dieter Zimmerling, Ludwigshafen, all of Fed. Rep. of Germany

[73] Assignee: BASF Aktiengesellschaft, Fed. Rep. of Germany

[21] Appl. No.: 717,108

[22] Filed: Mar. 28, 1985

[30] Foreign Application Priority Data

Apr. 3, 1984 [DE] Fed. Rep. of Germany ....... 3412295

[51] Int. Cl.$^4$ .......................... B01D 3/36; C07C 67/54
[52] U.S. Cl. ...................................... 203/96; 560/206; 560/218
[58] Field of Search ....................... 203/92, 93, 95–97; 560/206, 218

[56] References Cited

U.S. PATENT DOCUMENTS

| 2,807,573 | 2/1957 | Robertson | 203/96 |
| 3,214,347 | 10/1965 | Grekel et al. | 203/96 |
| 3,778,466 | 12/1973 | Matsuda | 560/206 |
| 4,332,966 | 6/1982 | Isogai et al. | 560/206 |
| 4,350,668 | 9/1982 | Isogai et al. | 560/206 |
| 4,360,692 | 11/1982 | Kummer et al. | 560/206 |

FOREIGN PATENT DOCUMENTS 007443  1/1982  Japan ................................. 560/218

*Primary Examiner*—Wilbur Bascomb
*Attorney, Agent, or Firm*—Keil & Weinkauf

[57] ABSTRACT

Methyl 4-pentenoate is isolated from mixtures containing this and methyl 3-pentenoate by a process in which from 0.25 to 0.4 part by weight of water is added per part by weight of methyl 4-pentenoate, and the azeotrope of methyl 4-pentenoate and water is distilled off.

2 Claims, No Drawings

ISOLATION OF METHYL 4-PENTENOATE FROM MIXTURES CONTAINING THIS AND METHYL 3-PENTENOATE

The reaction of butadiene with carbon monoxide and methanol in the presence of a cobalt carbonyl catalyst essentially gives methyl 3-pentenoate. However, for further reactions, for example for the preparation of methyl formylvalerate by hydroformylation, it is advantageous to start from methyl 4-pentenoate.

Methyl 4-pentenoate is obtained by, for example, isomerization of methyl 3-pentenoate in the presence of a complex of rhodium-triphenylphosphine and tin chloride, as described in Tetrahedron, 28 (1972), 5769–5777. The isomerization of methyl 3-pentenoate gives a mixture of methyl 4-pentenoate, methyl 3-cis- and 3-trans-pentenoate and methyl 2-cis- and 2-trans-pentenoate in equilibrium. Although methyl 4-pentenoate has a boiling point which is 7° C. lower than that of methyl 3-pentenoate, very technically complicated apparatus, such as columns with 100 separation stages and a reflux ratio of 50, is required in order to separate methyl 4-pentenoate from methyl 3-pentenoate.

It is an object of the present invention to simplify the isolation of methyl 4-pentenoate from methyl 3pentenoate and in particular to manage with a smaller number of separation stages and a lower reflux ratio in the distillation.

We have found that this object is achieved by a process for the isolation of methyl 4-pentenoate from a mixture containing this and methyl 3-pentenoate by distillation, wherein from 0.25 to 0.4 part by weight of water is added per part by weight of methyl 4-pentenoate, and the azeotrope of methyl 4-pentenoate and water is distilled off.

The novel process has the advantage that it is not very technically complicated and requires a smaller number of separation stages and a lower reflux ratio in order to separate the isomeric esters.

The novel process is noteworthy in that the methyl 4-pentenoate/water azeotrope boils at 91.5° C. whereas the methyl 3-pentenoate/water azeotrope boils at 93.5° C., so that the difference in boiling points is only 2° C. whereas the difference in the boiling points of the esters themselves is 7° C.

According to the invention, mixtures of methyl 4-pentenoate and methyl 3-pentenoate are used as the starting materials, these mixtures also containing, as a rule, methyl 2-pentenoate. Suitable mixtures contain, for example, from 3 to 15% by weight of methyl 4-pentenoate, from 75 to 95% by weight of methyl 3-pentenoate and from 0 to 10% by weight of methyl 2-pentenoate, and are obtained by, for example, isomerization of methyl 3-pentenoate or methyl 2-pentenoate at elevated temperatures in the presence of an acidic ion exchanger or an acidic zeolite which contains a noble metal of group eight of the periodic table. Preferably used catalysts are styrene/divinylbenzene copolymers containing sulfo groups, or acidic zeolites of the A, X or Y type in the H form, ie. in the acidic form. The acidic ion exchangers or acidic zeolites preferably contain from 0.01 to 1% by weight of palladium, ruthenium or rhodium, in particular palladium. The isomerization is carried out as a rule at from 100° to 150° C. The isomerization of methyl 3-pentenoate in this manner at 135° C. gives, for example, an isomer mixture consisting of 8% by weight of methyl 4-pentenoate, 91% by weight of methyl 3-pentenoate and 0.5% by weight of methyl 2-pentenoate.

The methyl 4-pentenoate present in the mixture is isolated from the latter by distillation, from 0.25 to 0.40 part by weight of water being added per part by weight of methyl 4-pentenoate, and the azeotrope of methyl 4-pentenoate and water being distilled off. The amounts of water fed in thus depend on the amount of methyl 4-pentenoate which is present in the starting mixture and which is required for formation of the methyl 4-pentenoate/water azeotrope with a water content of 28.6% by weight. The amount of water required can be added at the outset, but it is advantageous to add it continuously at the required rate during the distillation, for example at the rate at which the methyl 4-pentenoate/water azeotrope is removed at the top of the column. Preferably, the amount of water used does not exceed the amount appropriate for the methyl 4-pentenoate/water azeotrope.

The distillation is carried out, as a rule, in a conventional column, such as a packed column, a bubble tray column or a sieve tray column, the columns advantageously possessing from 20 to 60 trays. It has proven advantageous to maintain a reflux ratio of from 1:2 to 1:15 during the distillation. By adding water in a restricted amount, which is just sufficient for the formation of the methyl 4-pentenoate/water azeotrope, it is possible to separate this azeotrope selectively from the remaining methyl pentenoates. Methyl 4-pentenoate is obtained by separation of the resulting distillate into a methyl 4-pentenoate phase and a water phase, followed by decantation.

The procedure according to the invention can be carried out batchwise, but is advantageously effected continuously.

Methyl 4-pentenoates are useful for the preparation of δ-formylvalerates, which are intermediates for the preparation of caprolactam.

The Examples which follow illustrate the process according to the invention.

EXAMPLE 1

225 ml/hour of a mixture of 8% by weight of methyl 4-pentenoate, 91.7% by weight of methyl 3-pentenoate and 0.3% by weight of methyl 2-pentenoate are fed into a column which has a length of 80 cm and a diameter of 3 cm and is packed with 3 mm wire spirals. At the same time, 6 ml/hour of water are pumped in at the top of the column. The temperature at the bottom of the column is kept at 135°–137° C. At a reflux ratio of 1:10, 26 ml/hour of a mixture of water and methyl pentenoates are obtained, phase separation of this mixture giving 6 ml of water and 20 ml of pentenoates. According to analysis by gas chromatography, 90% by weight of methyl 4-pentenoate and 10% by weight of methyl 3-pentenoate are obtained.

COMPARATIVE EXAMPLE

The procedure described in Example 1 is followed, except that the addition of water is dispensed with. At a reflux ratio of 1:10, a mixture of methyl pentenoates containing 47% by weight of methyl 4-pentenoate is obtained at the top of the column.

We claim:

1. A process for the isolation of methyl 4-pentenoate from a mixture containing this and methyl 3-pentenoate, wherein from 0.25 to 0.4 part by weight of water is added to the mixture per part by weight of methyl 4-pentenoate, and the azeotrope of methyl 4-pentenoate and water is distilled off.

2. A process as claimed in claim 1, wherein the amount of water added does not exceed the amount appropriate for the azeotrope of methyl 4-pentenoate and water.